(12) United States Patent
McLaughlin et al.

(10) Patent No.: US 12,053,628 B2
(45) Date of Patent: Aug. 6, 2024

(54) MULTI-ELECTRODE ARRAY WITH UNITARY BODY

(71) Applicant: Micro-Leads, Inc., Somerville, MA (US)

(72) Inventors: Bryan L. McLaughlin, Cambridge, MA (US); Girish Chitnis, Watertown, MA (US); John Ogren, Antrim, NH (US)

(73) Assignee: Micro-Leads, Inc., Somerville, MA (US)

( * ) Notice: Subject to any disclaimer, the term of this patent is extended or adjusted under 35 U.S.C. 154(b) by 389 days.

(21) Appl. No.: 17/473,387

(22) Filed: Sep. 13, 2021

(65) Prior Publication Data

US 2021/0402176 A1 Dec. 30, 2021

Related U.S. Application Data

(63) Continuation of application No. 15/806,005, filed on Nov. 7, 2017, now Pat. No. 11,116,964.

(60) Provisional application No. 62/418,343, filed on Nov. 7, 2016.

(51) Int. Cl.
*A61B 5/00* (2006.01)
*A61N 1/05* (2006.01)
*A61N 1/36* (2006.01)

(52) U.S. Cl.
CPC ......... *A61N 1/0553* (2013.01); *A61N 1/0534* (2013.01); *A61N 1/0556* (2013.01); *A61N 1/0558* (2013.01); *A61N 1/36062* (2017.08)

(58) Field of Classification Search
CPC .................... A61N 1/0553; A61N 1/0558
See application file for complete search history.

(56) References Cited

U.S. PATENT DOCUMENTS

| 4,941,961 A | 7/1990 | Noguchi et al. |
| 5,417,719 A | 5/1995 | Hull et al. |
| 5,689,877 A | 11/1997 | Grill, Jr. et al. |

(Continued)

FOREIGN PATENT DOCUMENTS

| CA | 2448912 C | 1/2012 |
| CN | 102783942 A | 11/2012 |

(Continued)

OTHER PUBLICATIONS

Chinese Patent Office, First Office Action for Chinese Patent Application No. 201780075522.X, dated Nov. 22, 2022, 20 pages.

(Continued)

*Primary Examiner* — Michael J D'Abreu
(74) *Attorney, Agent, or Firm* — Nutter, McClennen & Fish, LLP

(57) ABSTRACT

An electrode array system includes a unitary body forming a plurality of apertures, and a plurality of continuous conductive elements at least partially encapsulated within the unitary body. The continuous conductive elements include/form a plurality of contacts, a plurality of electrode sites configured to couple with neural tissue (e.g., a spinal nerve or peripheral nerve), and a plurality of interconnects extending between the plurality of contacts and the plurality of electrode sites. The plurality of electrode sites are aligned with the plurality of apertures, and the plurality of apertures expose the plurality of electrodes.

14 Claims, 13 Drawing Sheets

(56) References Cited

U.S. PATENT DOCUMENTS

| | | |
|---|---|---|
| 6,024,702 A | 2/2000 | Versen |
| 6,871,099 B1 | 3/2005 | Whitehurst et al. |
| 7,012,192 B2 | 3/2006 | Stevenson et al. |
| 7,142,909 B2 | 11/2006 | Greenberg et al. |
| 7,211,103 B2 | 5/2007 | Greenberg et al. |
| 7,613,524 B2 | 11/2009 | Jordan |
| 7,697,995 B2 | 4/2010 | Cross, Jr. et al. |
| 7,749,608 B2 * | 7/2010 | Laude .................. H05K 3/185 428/209 |
| 7,846,285 B2 | 12/2010 | Zhou et al. |
| 7,877,866 B1 | 2/2011 | Greenberg et al. |
| 8,000,804 B1 | 8/2011 | Wessendorf et al. |
| 8,805,542 B2 | 8/2014 | Tai et al. |
| 9,002,459 B2 | 4/2015 | Lee et al. |
| 9,095,699 B2 | 8/2015 | Rosenberg et al. |
| 9,174,038 B2 | 11/2015 | Schuttler et al. |
| 9,364,660 B2 | 6/2016 | Howard et al. |
| 9,387,326 B2 | 7/2016 | Moffitt |
| 9,409,023 B2 | 8/2016 | Burdick et al. |
| 9,561,363 B2 | 2/2017 | Skubitz et al. |
| 9,572,976 B2 | 2/2017 | Howard et al. |
| 9,656,085 B2 | 5/2017 | Moffitt et al. |
| 11,116,964 B2 | 9/2021 | McLaughlin et al. |
| 2003/0233133 A1 | 12/2003 | Greenberg et al. |
| 2006/0257672 A1 | 11/2006 | Horikoshi et al. |
| 2007/0207569 A1 | 9/2007 | Greenberg et al. |
| 2011/0238145 A1 | 9/2011 | Swanson |
| 2011/0270067 A1 | 11/2011 | Faraji et al. |
| 2011/0270350 A1 | 11/2011 | Feler et al. |
| 2012/0006793 A1 | 1/2012 | Swanson |
| 2012/0245449 A1 | 9/2012 | Williams et al. |
| 2013/0060313 A1 | 3/2013 | Cross, Jr. |
| 2013/0345780 A1 | 12/2013 | Tabada et al. |
| 2014/0039241 A1 | 2/2014 | Jarvik |
| 2014/0128954 A1 | 5/2014 | Schuttler et al. |
| 2014/0172051 A1 | 6/2014 | Pannu et al. |
| 2014/0180361 A1 | 6/2014 | Burdick et al. |
| 2014/0180370 A1 | 6/2014 | Romero |
| 2014/0254124 A1 | 9/2014 | Raje et al. |
| 2016/0007874 A1 * | 1/2016 | Ma ....................... A61B 5/6868 600/377 |
| 2016/0158559 A1 | 6/2016 | Greenberg et al. |
| 2016/0192524 A1 | 6/2016 | Ruben |
| 2016/0213917 A1 | 7/2016 | Dalm et al. |
| 2016/0254080 A1 | 9/2016 | Shah et al. |
| 2017/0120056 A1 | 5/2017 | Woods et al. |
| 2017/0157390 A1 | 6/2017 | Howard et al. |
| 2017/0246452 A1 | 8/2017 | Liu et al. |
| 2018/0200505 A1 | 7/2018 | McLaughlin et al. |
| 2018/0213665 A1 | 7/2018 | Dittmer et al. |
| 2020/0215335 A1 | 7/2020 | McLaughlin et al. |

FOREIGN PATENT DOCUMENTS

| | | |
|---|---|---|
| CN | 103702714 A | 4/2014 |
| CN | 103813828 A | 5/2014 |
| CN | 104254365 A | 12/2014 |
| WO | 2007/039735 A1 | 4/2007 |
| WO | 2017/147151 A1 | 8/2017 |

OTHER PUBLICATIONS

**International Search Report—International Application No. PCT/US18/14566 dated Mar. 29, 2018, together with the Written Opinion of the International Searching Authority, 13 pages.

**International Search Report—International Application No. PCT/US19/68469 dated Mar. 25, 2020, together with the Written Opinion of the International Searching Authority, 11 pages.

*International Searching Authority, International Search Report—International Application No. PCT/US17/60408, dated Jan. 18, 2018, together with the Written Opinion of the International Searching Authority, 20 pages.

**Schuettler et al., "Fabrication of implantable microelectrode arrays by laser cutting of silicone rubber and platinum foil*," http://iopscience.iop.org/article/10.1088/1741-2560/2/1/013/pdf, Journal of Neural Engineering, Institute of Physics Publishing, vol. 2, No. 1, Feb. 22, 2005, pp. S121-S128.

**Schuettler et al., "Stretchable Tracks for Laser-Machined Neural Electrode Arrays," 31st Annual International Conference of the IEEE EMBS, Minneapolis, MN, USA, Sep. 2-6, 2009, pp. 1612-1615.

**Supplementary European Search Report for European Application No. EP 17866496.7, dated Jun. 3, 2020 (9 pages).

**U.S. Appl. No. 15/876,035, filed Jan. 19, 2018, Spinal Cord Stimulation Method to Treat Lateral Neural Tissues.

**U.S. Appl. No. 16/680, 171, filed Nov. 11, 2019, Implantable Devices with Welded Multi-Contact Electrodes and Continuous Conductive Elements.

* cited by examiner

MULTI-ELECTRODE ARRAY WITH UNITARY BODY

PRIORITY

This patent application is a continuation of U.S. patent application Ser. No. 15/806,005, filed Nov. 7, 2017, entitled, "MULTI-ELECTRODE ARRAY WITH UNITARY BODY," which claims priority from provisional U.S. patent application No. 62/418,343, filed Nov. 7, 2016, entitled, "MULTI-CHANNEL COUNT ELECTRODE ARRAYS WITH PERFORATED REINFORCEMENT AND PLANAR CONDUCTIVE ELEMENTS," and naming Bryan McLaughlin as inventor. The disclosures of each of the above-noted patent applications are incorporated herein, in their entireties, by reference.

GOVERNMENTAL SUPPORT

This invention was made with government support under W911NF-15-C-0007 awarded by US ARMY Contracting Command—Aberdeen (ACC-APG-RTP W911NF). The government has certain rights in the invention.

FIELD OF THE INVENTION

The invention generally relates to electrode arrays and, more particularly, the invention relates to implantable neural electrodes for neurostimulation devices.

BACKGROUND OF THE INVENTION

Electrical stimulation therapy commonly uses a number of modalities, such implantable arrays having electrodes connected with physiological neural tissue. To that end, during use, an implanted pulse generator directs prescribed signals to the electrodes for a desired therapeutic result. In addition, the generator may record neural information from the tissue to inform therapy delivery. When used for chronic pain in the spinal cord, for example, the implantable array often has a large number of electrical electrodes to enable spatially selective therapy to targeted volumes of neural tissue. This technique commonly provides effective pain relief therapy to specific full or partial dermatomes (e.g., an extremity such as the foot, leg, lower back, hand, etc.).

Those in the art often use multi-contact electrodes to deliver energy to small tissue volumes adjacent to each contact spaced 1) laterally across the spinal cord and 2) longitudinally at one or more vertebral levels. In other anatomies such as the retina, arrays of high-density electrodes enable finer spatial stimulation to improve the resolution of vision. In cortical anatomies, high-density electrodes can be used to focus stimulation to target volumes to provide therapy and eliminate stimulating unwanted areas known to cause off-target effects (loss of speech or memory). In spinal cord anatomies, high-density electrodes can be used to provide therapeutic access to numerous dermatomes where pain is experienced, which may be at different vertebral levels, nerve roots, or distinct positions across the spinal cord.

Undesirably, prior art arrays often suffer from robustness issues, which can cause them to break apart within a patient's body. This can cause the need for immediate medical treatment, potentially harming the patient.

SUMMARY OF VARIOUS EMBODIMENTS

In accordance with one embodiment of the invention, an electrode array system includes a unitary body forming a plurality of apertures, and a plurality of continuous conductive elements (e.g., a metal layer) at least partially encapsulated within the unitary body. The continuous conductive elements include/form a plurality of contacts, a plurality of electrode sites configured to couple with a neural tissue (e.g., the spinal nerve or a peripheral nerve), and a plurality of interconnects extending between the plurality of contacts and the plurality of electrode sites. The plurality of electrode sites are aligned with the plurality of apertures, and the plurality of apertures expose the plurality of electrode sites.

As a unitary design, the body preferably is seamless. Moreover, each contact may connect with at least one electrode by at least one interconnect.

The unitary body may be formed a material having a body tensile strength, while the electrode array system further includes a reinforcing material at least partly encapsulated by the unitary body. The reinforcing material may have a reinforcing tensile strength that is greater than the body tensile strength. Among other things, the reinforcing material may include a woven or braided structure and/or one in which multiple fibers are oriented in multiple directions. In a similar manner, the reinforcing material may include a polymer, nano or micro-particles or fibers, a hybrid or composite material, or other material with appropriate material properties. For example, the unitary body may be formed from vulcanized silicone, polyurethane, or other cured, dried, or set polymers.

The unitary body can be considered to have a top surface that forms the plurality of apertures. The plurality of electrode sites thus may be recessed below the top surface. Furthermore, the continuous conductive elements may be formed from a thin film or a foil.

The system may include a lead coupled with the plurality of contacts. This lead has a proximal contact array (at a generator port) configured to couple with a pulse generator. Accordingly, the system also may include a pulse generator having a lead port to which the contact array of the generator port couples.

In accordance with another embodiment of the invention, a method of fabricating an electrode array forms a first unvulcanized layer and a second unvulcanized layer, and patterns a conductive layer to produce a plurality of continuous conductive elements to form a plurality of contacts, a plurality of electrode sites, and a plurality of interconnects extending between the plurality of contacts and the plurality of electrode sites. The method further forms apertures in at least one of the first and second unvulcanized layers, couples the continuous conductive elements with one of the first and second unvulcanized layers, and couples together the first and second unvulcanized layers in a manner that at least partially encapsulates the continuous conductive elements. Next, the method vulcanizes the unvulcanized layers after coupling them together to form a flexible vulcanized unitary body. The plurality of apertures of the vulcanized unitary body expose the plurality of electrode sites.

Some embodiments form multiple layers of continuous conductive elements and form the unitary body from more than two unvulcanized layers.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an implantable electrode array has a robust construction that should more readily withstand expected forces within the human body. To that end, the implantable electrode array has a substantially unitary, fused body that encapsulates an internal metal layer. Having a unitary body eliminates weak bonding points, minimizing the likelihood that portions of the electrode array delaminate from one another. Details of illustrative embodiments are discussed below.

Active implantable systems provide therapy for a wide range of neurological, motor deficit, and cardiac diseases. For example, neurostimulator devices include spinal cord stimulation for the treatment of chronic pain, peripheral nerve stimulation for treatment of chronic pain, deep brain stimulation for depression or Parkinson's, and vagus nerve stimulation for epilepsy.

Figure 1:
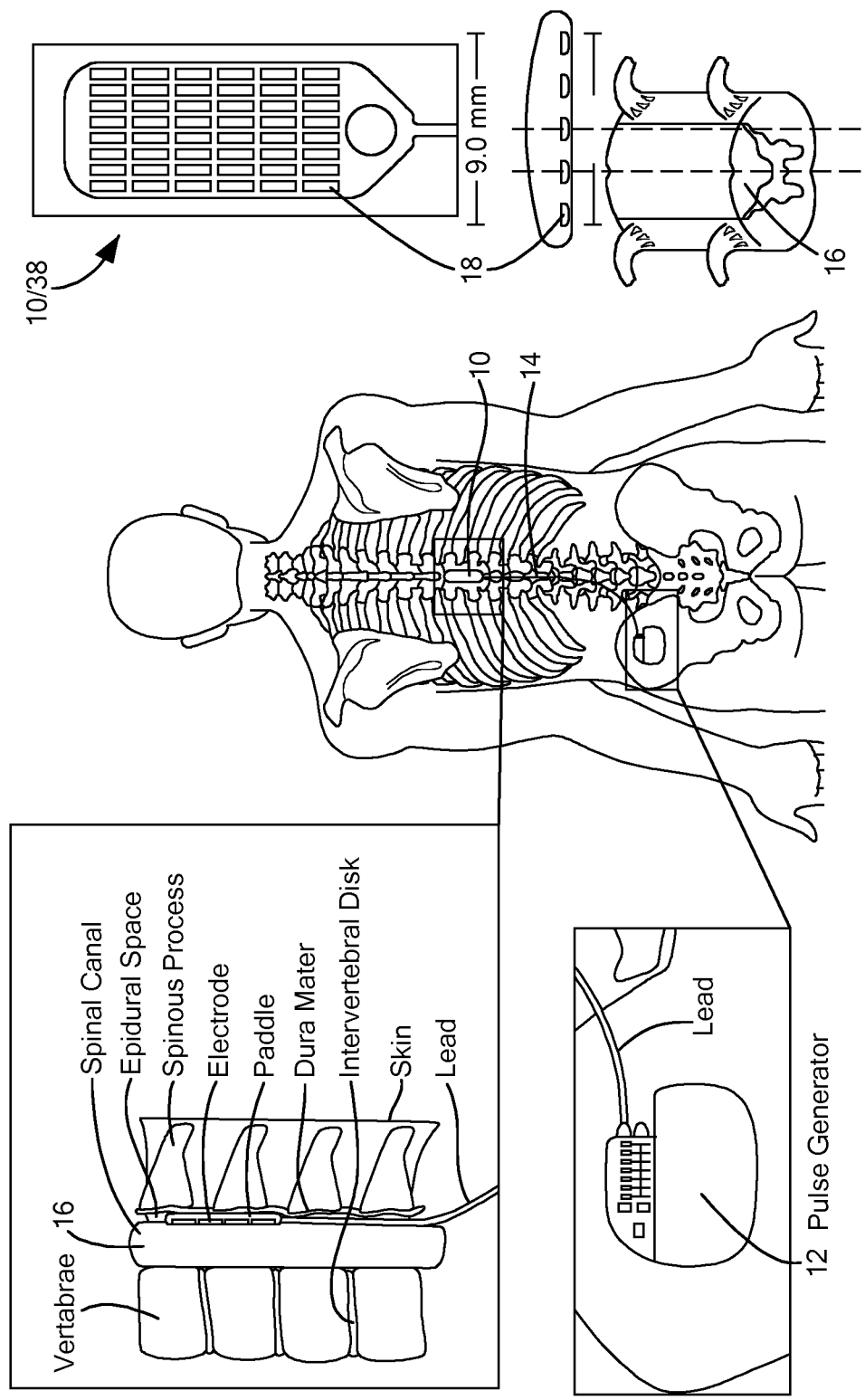
FIG. 1 schematically shows an example of one use of an implantable pulse generator and electrode array that may be configured in accordance with illustrative embodiments of the invention.
Figure 2:
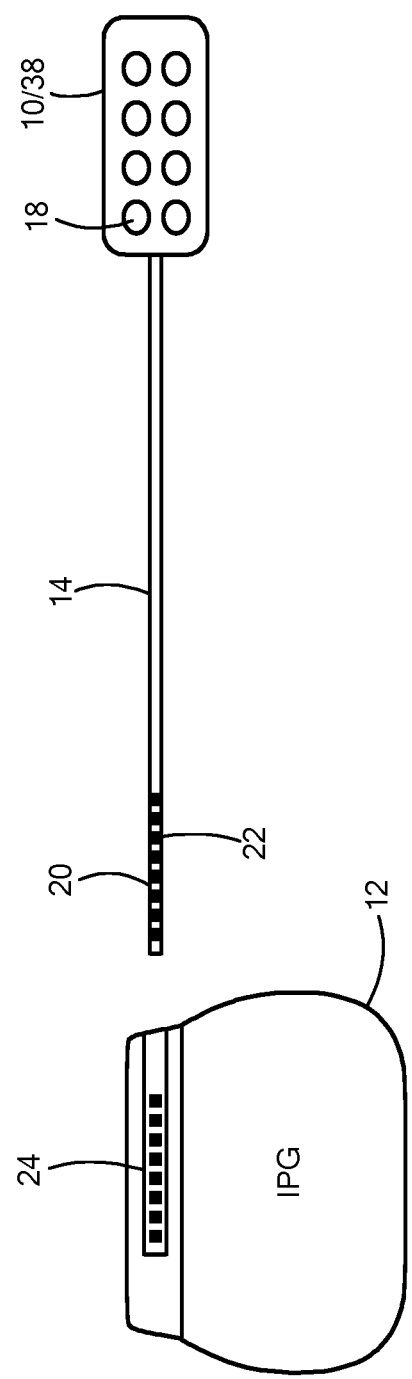
FIG. 2 schematically shows an electrode array system that may be configured in accordance with illustrative embodiments of the invention.

In spinal cord stimulation, an implantable pulse generator generates therapeutic pulses or waveforms for delivery through a therapy array/electrode array 10. FIG. 1 schematically shows an example of one use of an implantable pulse generator ("IPG 12") and electrode array 10 that may be configured in accordance with illustrative embodiments of the invention. For more clarity, FIG. 2 shows the IPG 12 and electrode array 10 outside of the body. As shown, FIGS. 1 and 2 depict an exemplary implantable pulse generator system/electrode array system with the noted IPG 12 to generate pulses, a lead 14 coupled with the IPG 12, and an implantable therapy array/electrode array 10 with nerve stimulation electrode sites 18. During use, the lead 14 may be positioned in the epidural space around the spinal cord 16 so that each stimulation contact 18 delivers therapy to a unique spatial location of the spinal cord 16. The lead 14 acts as an extension for a proximal connector plug 20 and ring-like contacts 22, which plug into a port plug 24 on the IPG 12. As noted below, the electrode arrays 10 may be formed into a variety of geometries, including a peripheral nerve cuff, spiral cuff, deep-brain cylindrical array and, paddle electrode arrays, etc.

The multi-contact array 10 has many electrode sites 18 exposed to the tissue, efficiently providing multiple points of electrical connection with the spinal cord 16 (including root entry zone, and roots). When electrical stimulation is applied through therapy electrode sites/electrode sites 18 to neural tissue (e.g., to spinal cord 16, peripheral nerves, ganglia, subthalamic nucleus, other brain tissue, or other neural tissue) and other biological tissue (e.g., cardiac, muscle, etc.), low-volume and precision technologies create multi-contact therapy arrays 10. Specifically, multi-contact arrays 10 improve therapy by selectively stimulating partial or sub-volumes of the neural tissue—by distributing stimulation energy (via cathodes and anodes) across one or more electrode sites 18 in proximity with the neural structure. In one embodiment, the multi-contact electrodes enable therapy to be precisely delivered to a sub-volume of the neural target (e.g., specific columns of the spinal dorsal column, particular dorsal root entry zone, dorsal root ganglia, one or more fascicles within a peripheral nerve, ganglia, etc.).

Conventional implantable multi-contact electrode arrays known to the inventors are assembled from non-continuous conductive elements (discrete metal contacts, discrete wires, etc). After the non-continuous conductive elements are connected (e.g., using welding, swaging, or crimping) and placed in a fixture, injection molding techniques position the conductive elements within an insulating elastomer. Conventional approaches, however, undesirably do not scale to ultra-thin (<1 mm), low-profile geometries. In particular, conventional injection molded electrodes assemblies are inherently thick (about 2 mm) due to the bulk volume required for the components and to facilitate the flow of encapsulation during the assembly process. Assembling non-continuous conductive elements and their density limitations of positioning and welding individual contacts and wires also limits these approaches from scaling to more than 16 or 32 electrical contacts.

Micro-fabrication techniques (e.g., photolithography, sputtering, liftoff, and etching) can produce ultra-thin continuous conductive elements (<2 micrometers) on ultra-thin substrates (<20 micrometers). However, thin-film continuous conductive elements are inherently brittle and fracture upon flexure and strain. Under normal handling and mechanical forces encountered within an implanted environment, the thin-conductor may fracture if stretched only up to about 10%. In contrast, elastomer layers used in these applications may stretch 50 percent to 2,000 percent, far exceeding the noted conductive layer limit. The thin-conductors absorb the tensile forces and, frequently, fracture over time.

Further, thin-film polymer substrate materials (e.g., Parylene C, Parylene H, Polyimide, etc.) are unproven in long-term human use electrodes due to their inherent mechanical instability. For example, thin-film polymer substrates suffer from mechanical and electrical instability during long-term aging tests. Specifically, the layers in the substrate are adhesively bonded (in contrast to welding), which fatigues over time, resulting in delamination and loss of insulation between electrodes. Such polymer substrates also have a stiffness approximately 10 times higher than neural tissue, often resulting in neural tissue injury, inflammatory reactions, scar tissue formation around the electrode, and reduction or loss of electrical stimulation therapy due to the encapsulation.

Hybrid elastomer electrodes have also been developed by coating a thin elastomer base substrate, and subsequently 1) attaching a laser-patterned metal conductor layer to the substrate, and 2) coating a thin top elastomer layer, which adhesively bonds to the base substrate. The adhesive bonds used to join the elastomer substrate layers are significantly weaker than the substrate elastomer material (bound together by fusion or welded bonds). The long-term deterioration of the adhesive bonds often leads to delamination between insulating layers in an implanted environment, a loss of isolation and function of the electrode, and eventual loss of therapy. Additionally, thin-conductor materials are fragile under repetitive mechanical stress (stretch, bend, and twisting), causing conductor failure leading to loss of delivery of therapy. To provide resilience to mechanic stress, additional polymer reinforcement material have been added to elastomer substrate stack to balance the mechanical mismatch. Upon stretch, the polymer reinforcement is proportionally strained, thereby preventing the conductors from solely absorbing the strain. However, polymer-elastomer substrates required more complex manufacturing steps, such as the steps of adding the polymer layer and encapsulating the polymer layer to prevent delamination.

In a similar manner, joining the layers using adhesive bonding between dissimilar elastomer and polymer materials produces poor adhesion between layers, which often causes delamination. Specifically, delamination 1) separates insulating materials from each other and the conductive features and 2) causes the electrode to fail to sense signals or deliver stimulus. These undesirable results lead to a loss of therapy.

To affix the conductors in position, the noted substrate layer of prior art hybrid elastomer electrodes is vulcanized. Subsequent steps utilize an additional top layer of elastomer, which is joined using an adhesive bond (the base layer is already cured requiring a wet top layer to adhesively bond). Undesirably, such a continuous adhesive bond between assembled layers produces a weak point—a seam—which often results in long-term delamination at the bond interface (see the seam 44 of FIG. 5).

The hybrid elastomer assembly approach has further limitations. For example, application of a continuous wet elastomer contaminates the electrode contacts or conductive contacts. After the substrates are adhesively bonded and vulcanized, the conductive elements are completely encapsulated with no openings or recesses to make electrical connections or to form an electrical connection to tissue. It therefore is then necessary to create openings in the elastomer, and to remove the elastomer that has contaminated the conductive contacts in these areas. An ablative process may serve this purpose (e.g., laser ablation or etching), undesirably exposing ashing residues to the conductive features. In addition to being costly and time-consuming, the residual ashing and debris produced by the ablation process requires extensive cleaning procedures to remove.

Figure 3:
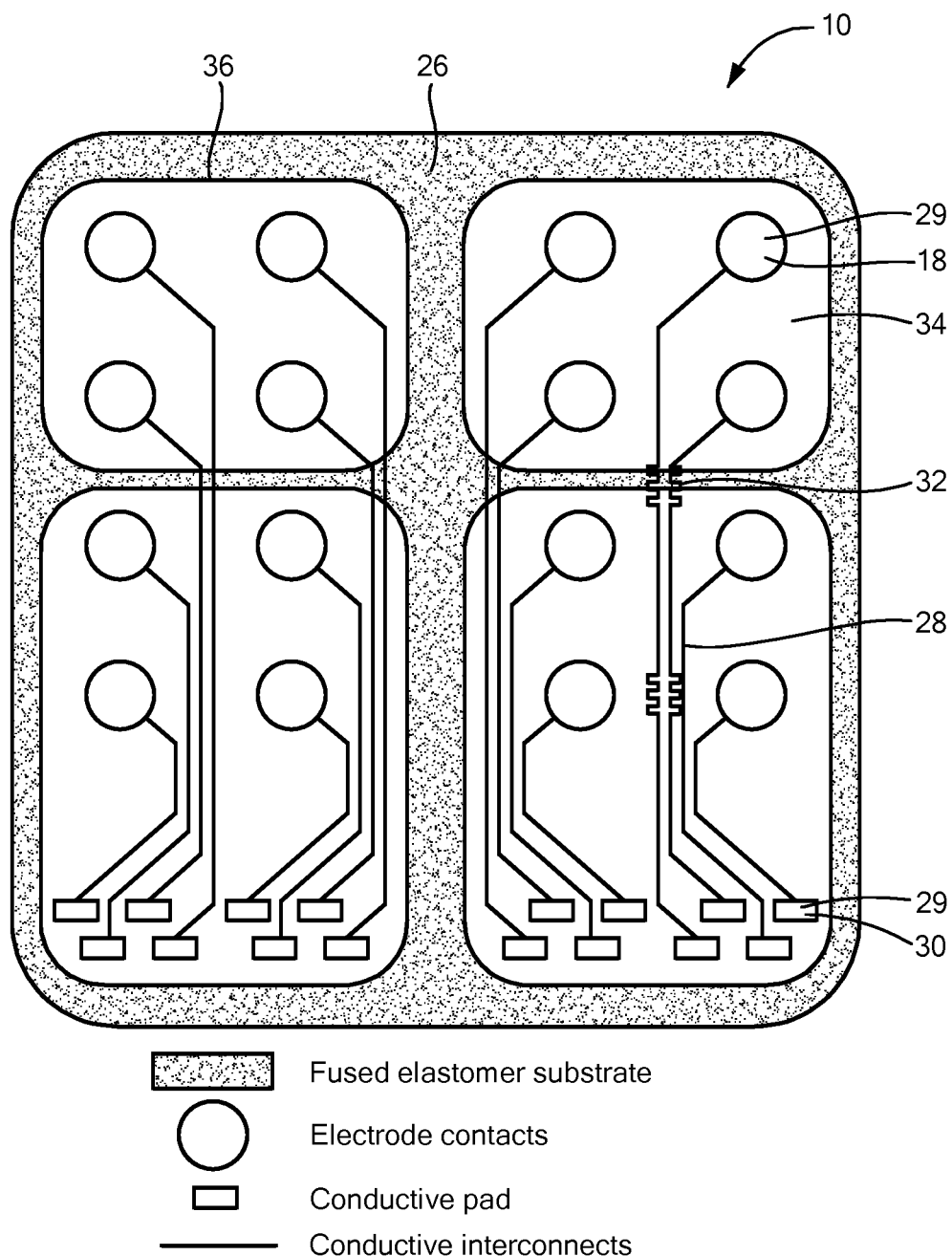
FIG. 3 schematically shows a plan view of an electrode array configured with in accordance with illustrative embodiments of the invention.

Recognizing these problems, the inventors developed an implantable, multi-electrode array 10 without significant weak points (e.g., seams). Instead, the array has a body that is integral/fused—a single continuous structure or body. To that end, FIG. 3 schematically shows a plan view of an implantable, multi-electrode array 10 configured with in accordance with illustrative embodiments of the invention. As shown, the implantable multi-electrode array 10 (e.g., for neuromodulation, cardiac stimulation, cardiac mapping, neural recording, etc.) has a fused, unitary, ultra-thin electrode substrate 26 fabricated with a mechanical robustness that can better withstand its implanted environment. In other words, the substrate 26 may be considered to be one piece—with no seams (as noted above). This substrate 26 also may be referred to as a "body 26."

Illustrative embodiments of the electrode array 10 include micro-scale continuous conductive elements, such as electrode sites 18, interconnects 28, conductive contacts 30, and strain relief features 32 that enable high-density implantable therapy arrays 10. The multi-contact electrode array 10 may have a small number of electrodes, or a large number of electrodes (e.g., greater than 16 electrodes) within the noted singular, unitary, fused, ultra-thin substrate 26.

The electrode array 10 includes an electrode site 18 with a conductive surface for delivering electrical stimulation to body tissue. The conductive interconnects 28, within the substrate 26, transmit electrical current from the conductive contacts 30 to the electrode sites 18, which also may provide the interface/bonding sites to the lead 14 (FIG. 2). Elastomeric material 34 electrically insulates the conductive interconnect 28, conductive contacts 30, and the body tissue to prevent short circuits and ensure that unintended electrical current does not leak into or otherwise interact in an unintended manner with the body tissue. To improve robustness, the interconnect 28 may be configured in a serpentine pattern to form the noted strain relief features 32, enabling the interconnects 28 to flex when subjected to certain expected forces (e.g., a longitudinal force exerted on the electrode array 10).

In accordance with illustrative embodiments and as noted below, a reinforcing material 36 (FIGS. 6A and 6B, discussed below) embedded within a base and/or cover elastomer layer mechanically strengthens the electrode array substrate assembly 26 without increasing rigidity or appreciable thickness. Among other things, this reinforcing material 36 includes open areas, pores, strips, or apertures to allow elastomers to continuously encapsulate (e.g., microfiber, woven mesh, honeycomb, carbon fiber).

Illustrative embodiments form the substrate 26 by fusing at least one discrete upper elastomer layer 34 (referred to as a "cover" or a "cover layer") and at least one discrete lower elastomer layer 34 (referred to as a "base" or a "base layer"). As discussed below with regard to FIG. 11, the elastomer layers 34 are prepared and spatially patterned in an unvulcanized material state, enabling subsequent elastomer fusion to form the single, unitary (i.e., integral, integrated, etc.) substrate 26 containing conductive elements. This fused substrate 26 overcomes delamination failure modes experienced between adhesively-joined layers of conventional approaches. As such, the unvulcanized material exists in the uncured, partially-cured, or "wet" state in which the material retains the ability to be formed or joined. Among other things, the unvulcanized material may include elastomers (e.g., silicone), polyurethanes (e.g., Pellethane, Tecothane) or other polymers. As an example, the unvulcanized material may include the first and second unvulcanized layers comprise thermoplastic polyurethane. When vulcanized (discussed below), the two layers together form a thermoplastic-polyurethane bond. In illustrative embodiments, the process chemically bonds the base and cover together.

The electrode sites 18 and interconnects 28 preferably are formed from a thin, continuous conductor material, such as a substantially flat, thin continuous metal conductor layer (e.g., a metal film or metal foil), with insulating elastomer material 34 on each side of the continuous conductive elements. For additional robustness, the continuous conductive elements may contain anchor features, such as slits, hooks, or holes, enabling insulating elastomer layers 34 to anchor the continuous conductive elements to the elastomer.

To further increase the number of electrode sites 18 and their density, the electrode array substrate 26 also may include more than one layer of continuous conductive elements. For example, the substrate 26 may have two continuous conductive element layers and three elastomer layers, increasing the contact density. In a manner similar to other embodiments, this embodiment also has a unitary, fused substrate 26 and optionally may have a reinforcement material/layer 36 to improve its mechanical properties without increasing its rigidity or appreciable thickness.

In illustrative embodiments, the continuous conductive elements are formed from metal, such as a metal film or a metal sheet (e.g., foil). Other embodiments, however, may form the continuous conductive elements from a conductive polymer, or a hybrid material. Several examples of hybrid materials may include a polymer having internal metal, carbon nanotubes, conductive ink, conductive epoxy, or other conductive materials.

Figure 4:
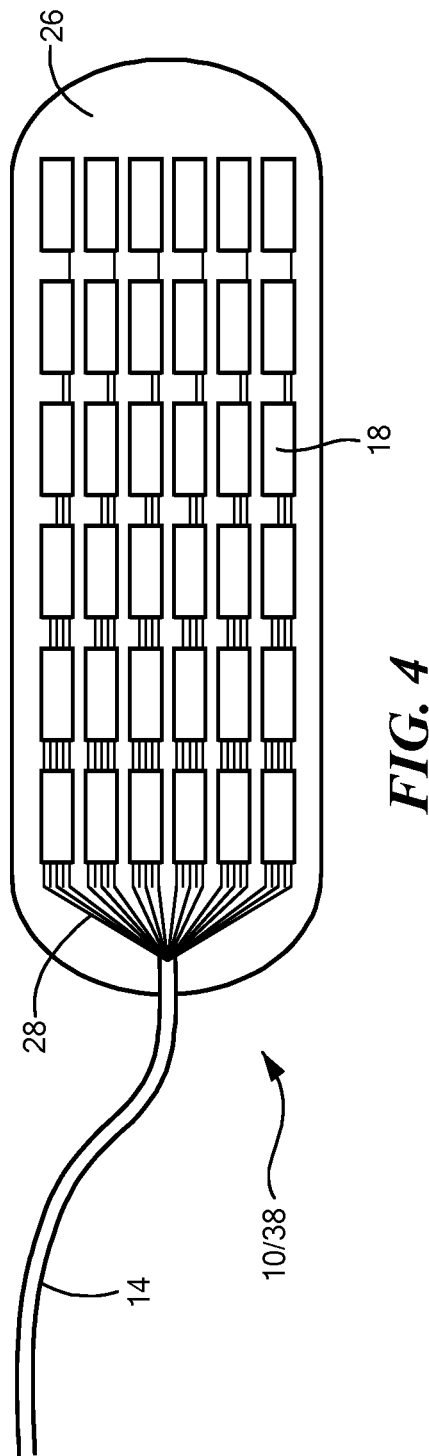
FIG. 4 schematically shows a plan view of another electrode array configured in accordance with other embodiments of the invention.

The array 10 may be arranged in any of a variety of different form factors. For example, FIG. 4 shows one implementation in which the electrode array 10 is arranged in a paddle configuration/assembly 38. As with some other embodiments, this paddle assembly 38 has continuous conductive element electrode sites 18 and conductor interconnects 28, and the lead 14 is permanently attached to the paddle assembly 38.

Figure 5:
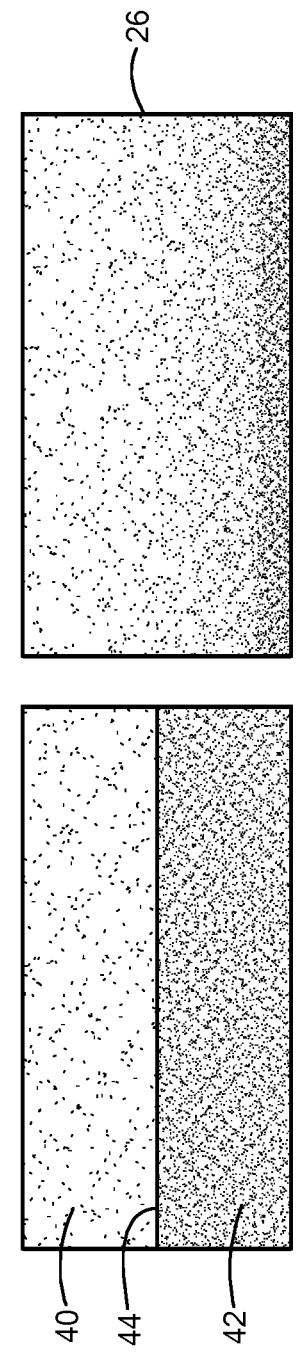
FIG. 5 schematically shows a cross-sectional view of a fusion bond in a substrate configured in accordance with illustrative embodiments of the invention.

FIG. 5 schematically compares a prior art adhesively bonded substrate assembly against the unitary, fused substrate 26 of illustrative embodiments. As shown, the adhesively bonded substrate has two distinct layers 40 and 42 that intersect/bond at an interface or seam 44. The fusion bonded substrate 26 of FIG. 5, however, is a single structure with no seams 44 (e.g., a continuous transition of material).

Figure 6A:
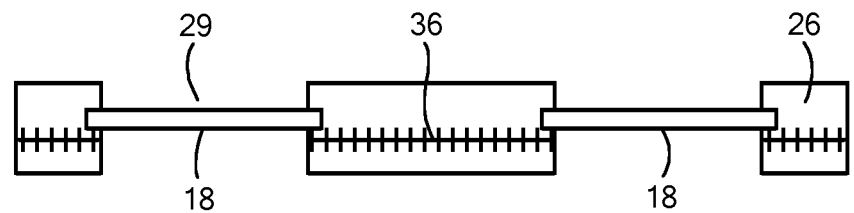
FIGS. 6A 6B, and 6C schematically show cross-sectional views of a fusion bond substrate configured in accordance with illustrative embodiments of the invention.
Figure 6B:
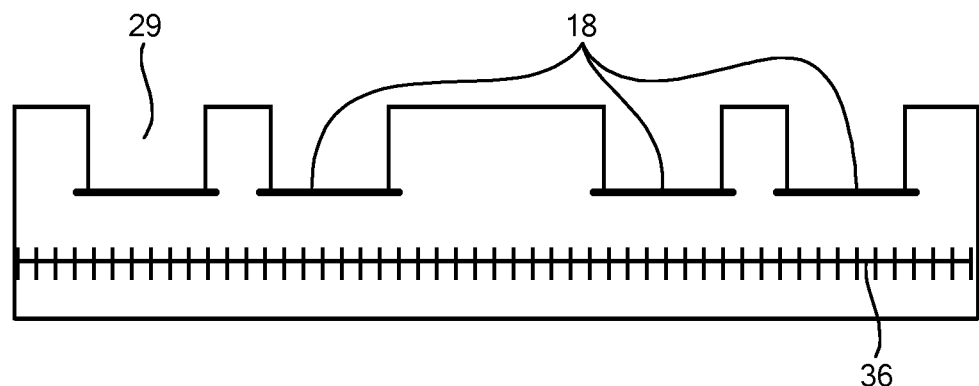
Figure 6C:
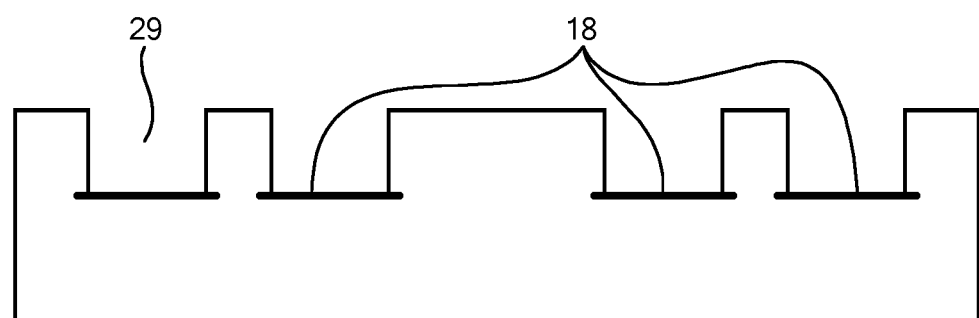

FIGS. 6A 6B, and 6C schematically show cross-sectional views of a fusion bonded substrate 26 configured in accordance with illustrative embodiments of the invention. FIG. 6A shows the substrate 26 as having openings/apertures 29 both on its top and bottom surface, while FIGS. 6B and 6C show the substrate 26 as having openings/apertures 29 only on one surface. FIGS. 6A and 6B also show the substrate having a reinforcement material whereas FIG. 6C does not contain a reinforcement material.

Additionally, to improve resilience to mechanic stress, illustrative embodiments of FIGS. 6A and 6B include one or more types of polymer reinforcement materials 36 within the substrate 26. To aid in protecting the integrity of the device for an implanted environment, the reinforcing material 36 preferably has mechanical properties that are greater than that of the elastomer forming the substrate 26 and yet, do not increase rigidity or add appreciable thickness. For example, the reinforcing material may contribute no more than about 10 percent to the maximum total thickness. In some embodiments, the reinforcing material 36 adds no net thickness because of its integration within the unitary body 26. When stretched, the polymer reinforcing material 36 is proportionally strained, thereby preventing the conductors from solely absorbing the strain.

Figure 7:
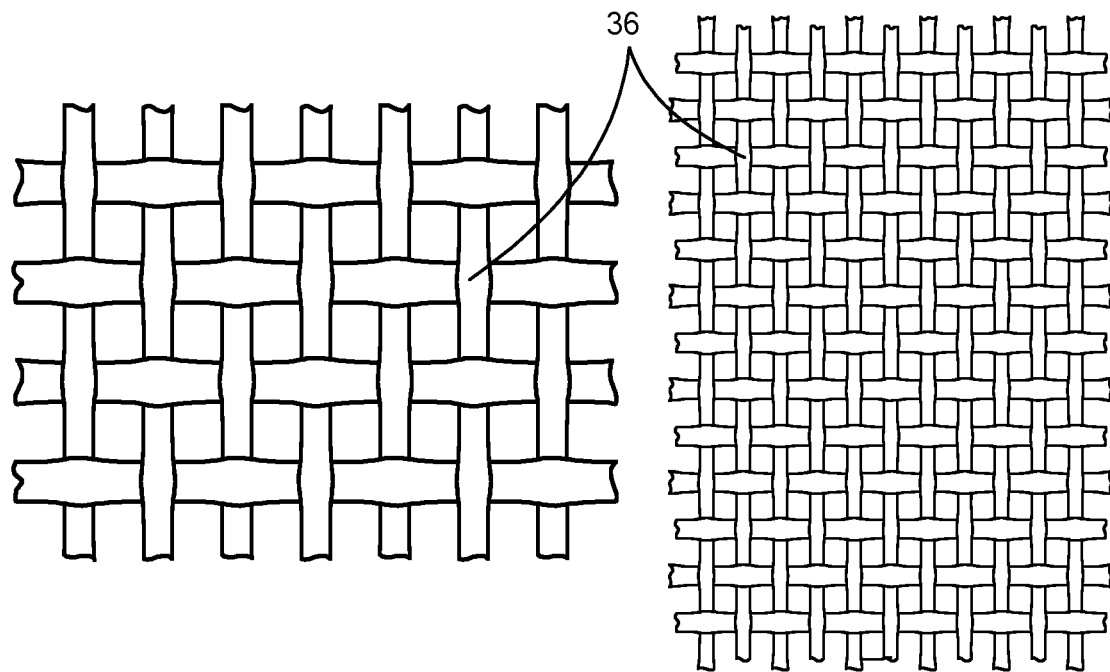
FIG. 7 schematically shows reinforcement material configured in accordance with illustrative embodiments of the invention.

FIG. 7 shows one embodiment of the reinforcing material 36. As shown, the reinforcing material 36 may be formed from one or multiple types of materials (e.g., micro-fiber, woven mesh, honeycomb, carbon fiber) arranged as an array of open areas. Accordingly, these open areas allow an elastomer to contiguously permeate through the reinforcing material 36. The fibers themselves preferably have a specified small fiber diameter (e.g., less than 500 micrometers diameter fibers). The right drawing of FIG. 7 shows a close up view of one implementation of the reinforcing material 36. Other embodiments may not be woven as in FIG. 7. For example, a layer with openings 29 may suffice in certain applications. Those skilled in the art may form the form the reinforcing material 36 in other ways. For example, micro/nano-fibers could also be embedded within the elastomer to reinforce the substrate.

To accomplish its function, the reinforcing material 36 preferably has material properties tuned to those of the unitary body 26. In illustrative embodiments, the reinforcing material 36 has a tensile strength that is greater than that of the unitary body 26. In related embodiments, the reinforcing material 36 has a tear strength that is greater than that of the unitary body 26. Those skilled in the art may configure the body 26 and the reinforcing material 36 to have one or more of these or other relative material properties (e.g., elongation).

Figure 8:
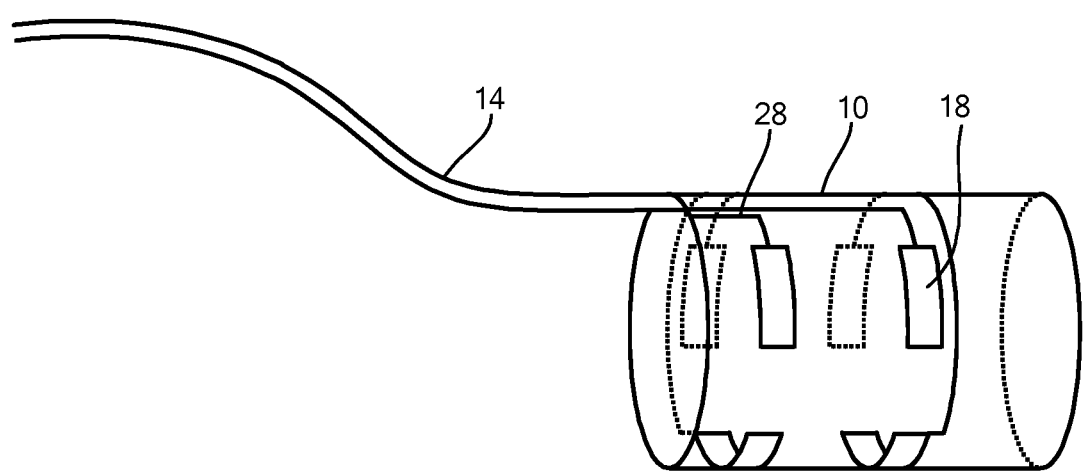
FIG. 8 schematically shows a multi-contact cuff electrode therapy electrode array configured in accordance with illustrative embodiments of the invention.

As noted above, the electrode array 10 may take on a number of different form factors. For example, FIG. 8 schematically shows an illustrative embodiment of the electrode array 10 taking on the form of a nerve cuff therapy electrode array (e.g., a cuff or spiral electrode array). As with other embodiments, this embodiment has continuous conductive elements of interconnects 28 and electrode sites 18. In use, this form factor may wrap around a nerve so that the electrodes electrode sites 18 face inwardly toward the peripheral nerve fibers. The continuous conductive elements, which includes electrode sites 18 and interconnects 28, are specifically formed to create the conformal geometry around a nerve.

Figure 9A:
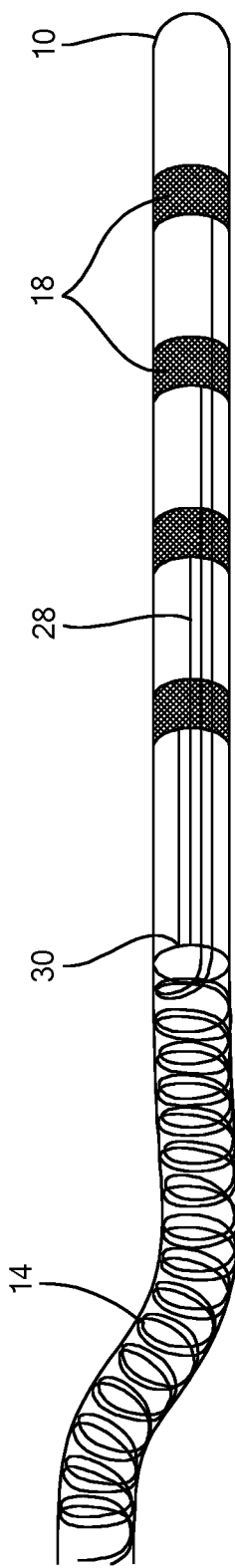
FIGS. 9A and 9B schematically show additional implementations of a cylindrical therapy electrode array configured in accordance with illustrative embodiments of the invention.
Figure 9B:
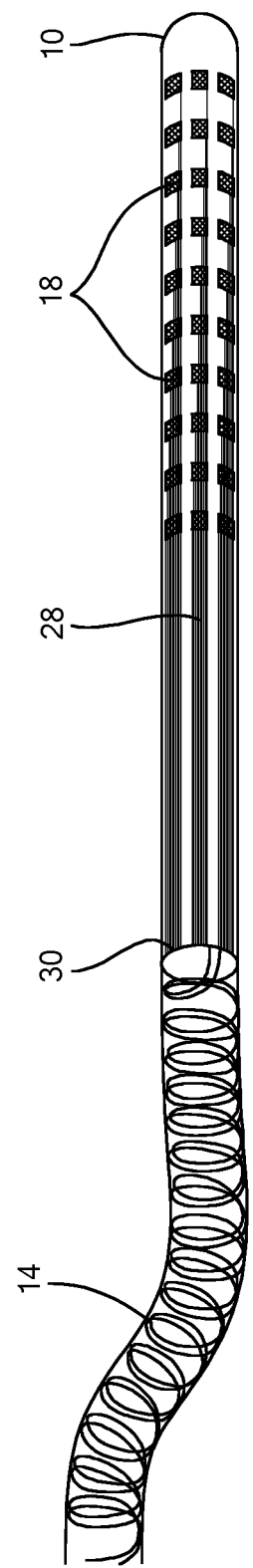

FIGS. 9A and 9B show other form factors. Specifically, FIG. 9A schematically shows a cylindrical electrode therapy array 10 having continuous conductive elements, including electrode sites 18 and interconnects 28, which have been curved to create the desired cylindrical geometry. The electrical electrode sites 18 face outwardly for delivering therapy to a volume of tissue. The lead 14 preferably contains helically coiled conductors connected at the conductive contacts 30 to the multi-contact therapy electrode array 10.

FIG. 9B schematically shows a related embodiment in which the high-density cylindrical electrode array 10 has continuous conductive elements with electrode sites 18 and interconnects 28 that have been curved to create a similar cylindrical geometry. In a manner similar to the embodiment of FIG. 9A, the high-density electrical electrode sites 18 face outwardly for delivering therapy to a volume of tissue. The lead 14 contains helically coiled conductors connected at the conductive contacts 30 to the multi-contact therapy array 10.

Figure 10:
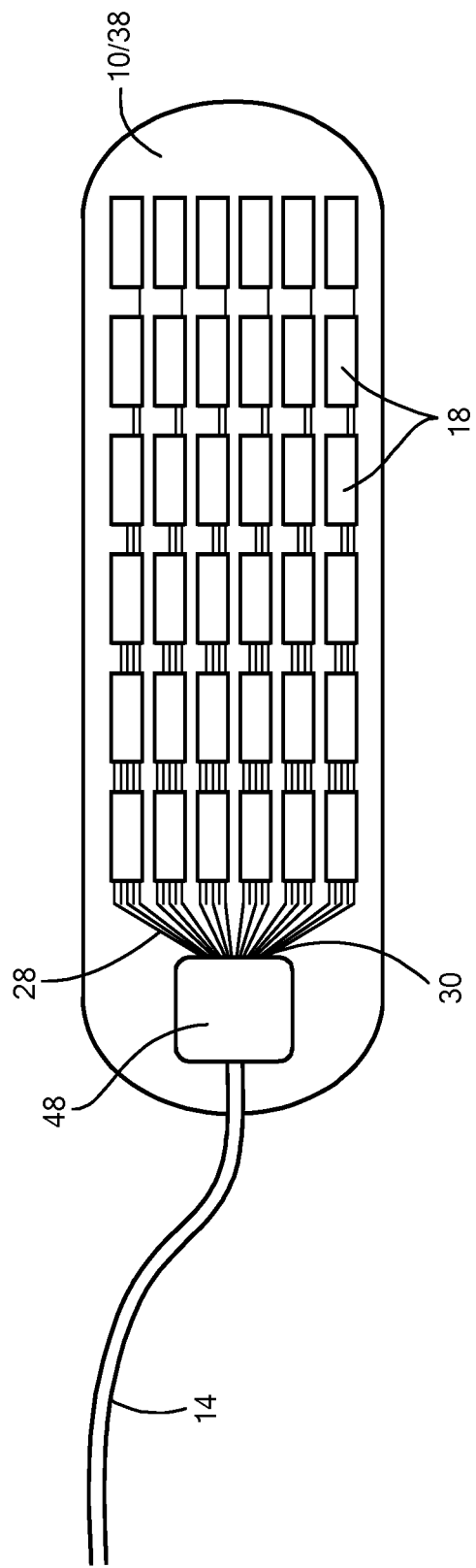
FIG. 10 schematically shows a plan view of an illustrative electrode array with active electronics embedded within its geometry.

Some embodiments may integrate active or passive electronics into the electrode array 10 (e.g., switching electronics, components making to improve systemic tolerance to magnetic resonant imaging, etc.). To that end, FIG. 10 schematically shows the high-density paddle assembly 38 with its conductive electrode sites 18 and interconnects 28 formed to create the planar geometry as a paddle assembly 38. Unlike prior embodiments, this paddle assembly 38 also has an active electronics circuit module 48 connected to the continuous conductive elements for switching current flow to the individual electrode(s). The lead 14 contains helically coiled conductors that are connected at the conductive contacts 30 to the electrode array 10. Note that other embodiments also may have the active electronics circuit module 48. Alternatively, the module 48 can have passive circuitry in addition to or instead of active circuitry. In some embodiments, rather than being in one location, the circuitry of the module 48 may be distributed across the electrode array 10.

Indeed, illustrative embodiments may use other form factors not discussed. Accordingly, discussion of specific form factors, such as the noted paddle and cylindrical form factors, are illustrative and not intended to limit additional embodiments.

Figure 11:
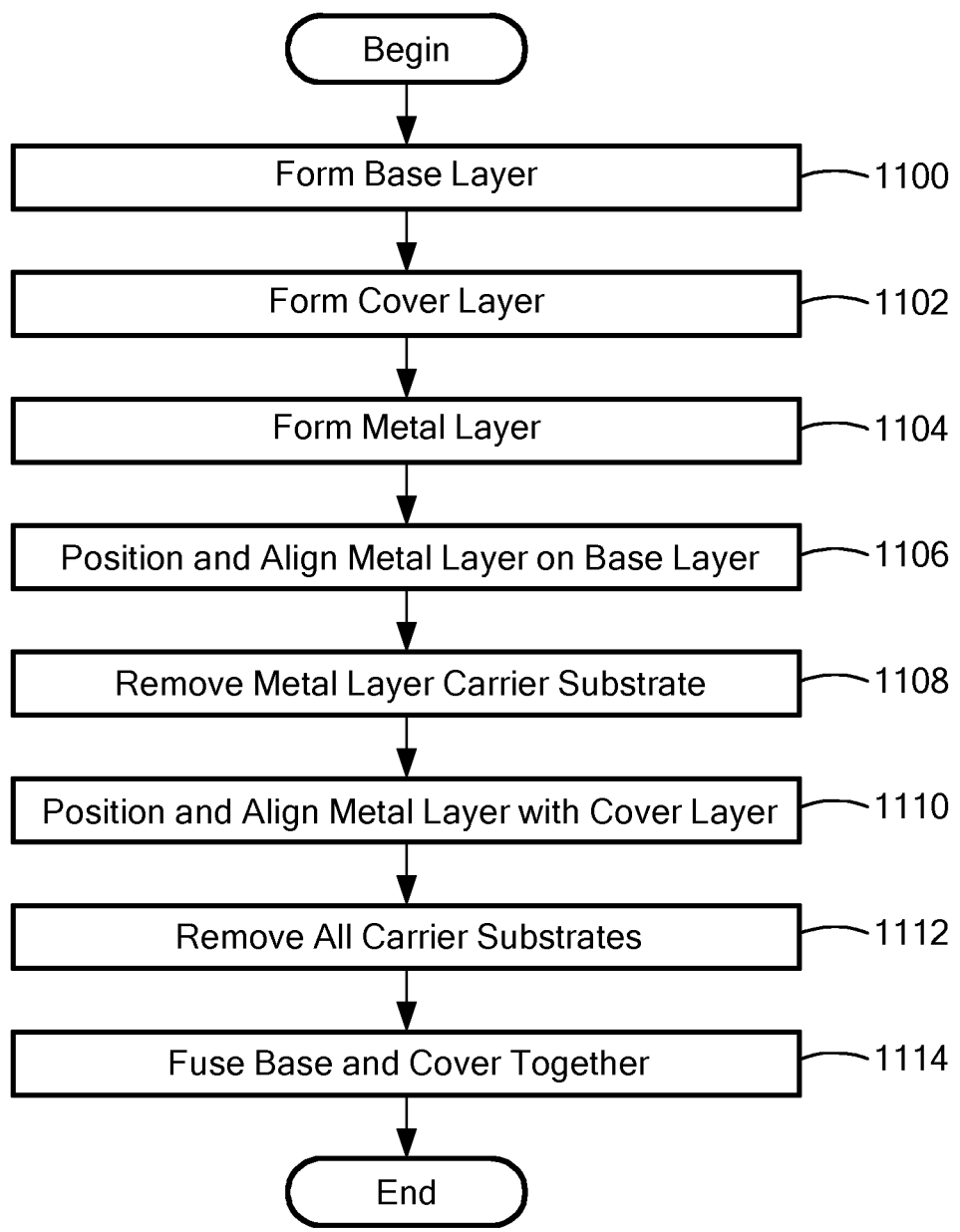
FIG. 11 shows a process of forming an electrode array in accordance with illustrative embodiments of the invention.

FIG. 11 shows a process of forming the above noted electrode array 10 in accordance with illustrative embodiments of the invention. It should be noted that this process is substantially simplified from a longer process that normally would be used to form the electrode array 10. Accordingly, the process of forming the electrode array 10 may have many other steps, such as testing steps or etching steps, which those skilled in the art may use. In addition, some of the steps may be performed in a different order than that shown, or at the same time. Those skilled in the art therefore can modify the process as appropriate. Moreover, as noted above and below, many of the materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

Figure 12:
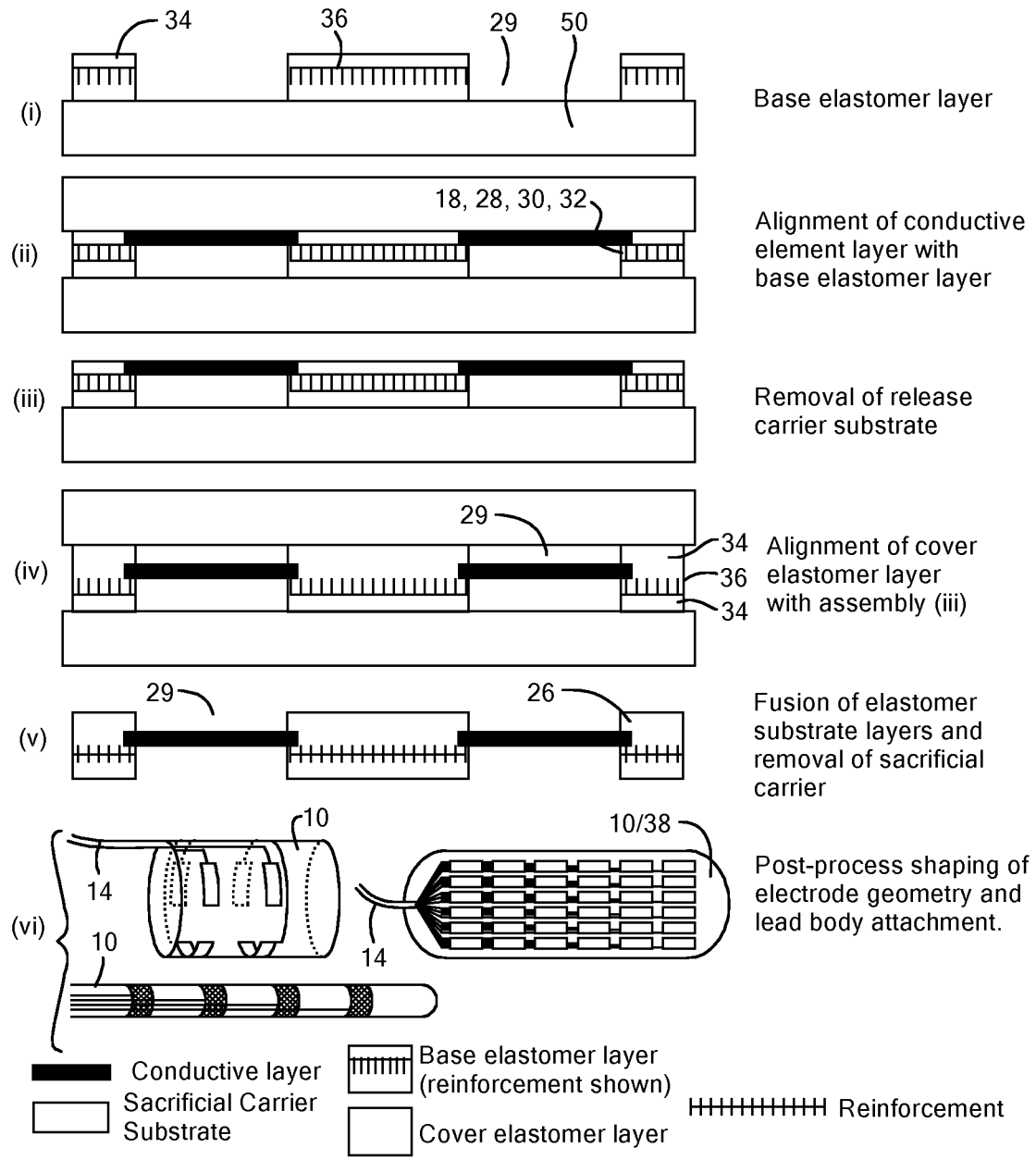
FIG. 12 graphically shows the entire electrode array as is assembled in accordance with illustrative embodiments of the invention.

To help understand FIG. 11, FIG. 12 schematically shows some of the steps of the process of FIG. 11. In fact, FIGS. 13 and 14 also schematically show some of the processes used to complete some of the steps in FIG. 11.

Figure 13:
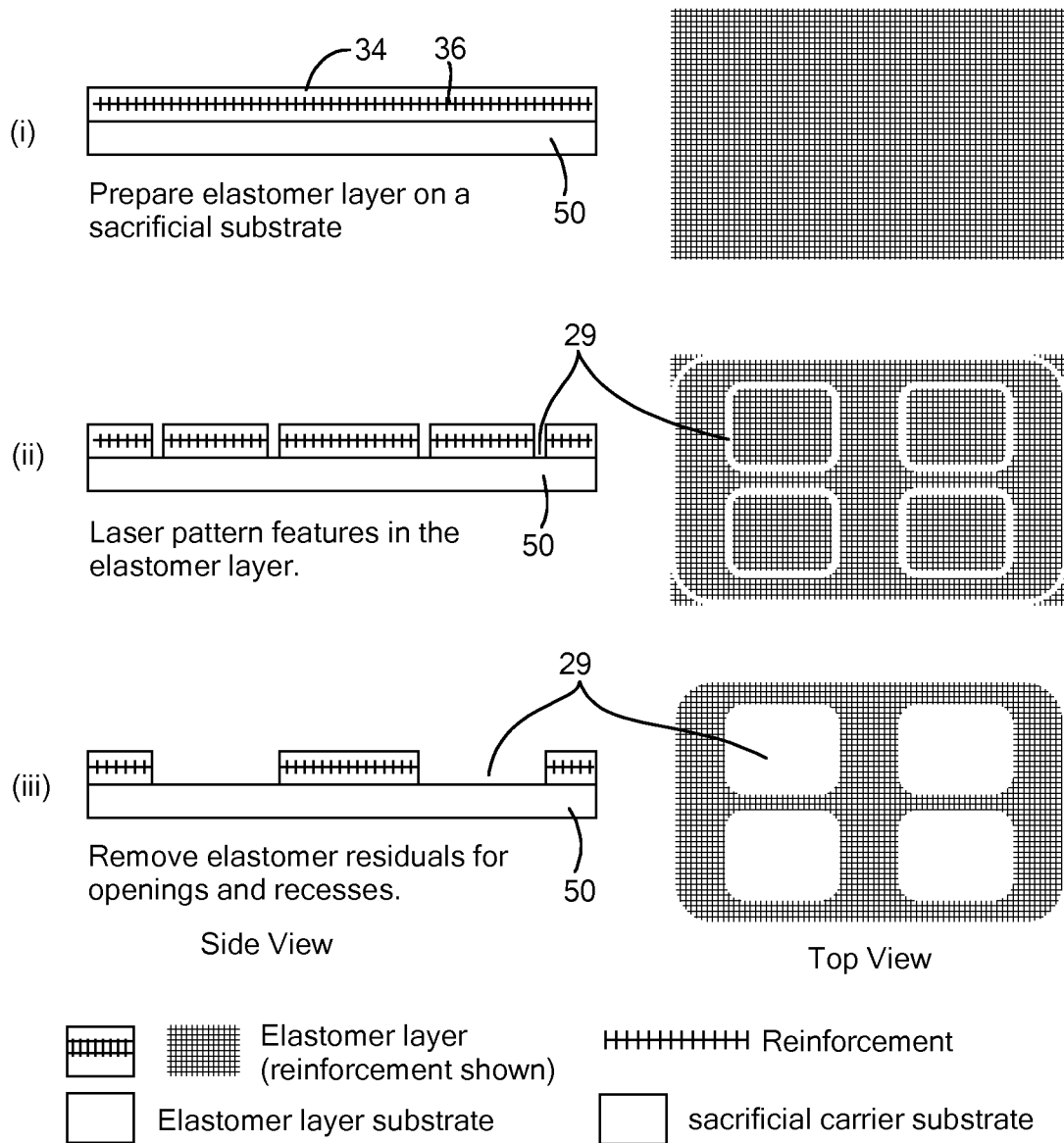
FIG. 13 graphically shows a reinforced electrode base layer as it is formed in accordance with illustrative embodiments of the invention.

The process of FIG. 11 begins at step 1100, which forms the base layer. To that end, FIG. 13 schematically shows a process of forming a base layer in accordance with illustrative embodiments of the invention. As shown at step (i) of FIG. 13, an ultra-thin elastomer substrate layer may be deposited on a sacrificial/carrier substrate 50 in an unvulcanized state. Then, as shown at (ii), the unvulcanized elastomer substrate layer may be processed, such as by using a laser to cut or form openings 29, recesses and/or other features. For example, those features may include the perimeter shape and curvature, holes to expose conductor electrode sites 18 to tissue, and holes to facilitate lead wires or feed-throughs. They also may include a feature outline, openings 29 for electrodes, and alignment holes. In preferred embodiments, a patterning process (e.g., a spatial patterning process, such as laser ablation) cuts the openings 29 while the elastomer layer is in an unvulcanized state. Elastomer material residuals not removed by the laser-patterning process may be manually removed (step iii). In alternative embodiments, after vulcanization, the process may form the openings 29, holes, apertures, etc.

After the elastomer residuals are removed from the assembly, the assembly forms an unvulcanized, patterned elastomer base layer. The openings 29 and recesses in the elastomer provide a conductive path for the electrical stimulation energy to pass from the electrode sites 18 to the tissue. The openings 29 have rims that are just above the top surfaces of the electrode sites 18. Thus, the electrode sites 18 are slightly recessed relative to the rims of the openings 29.

Figure 14:
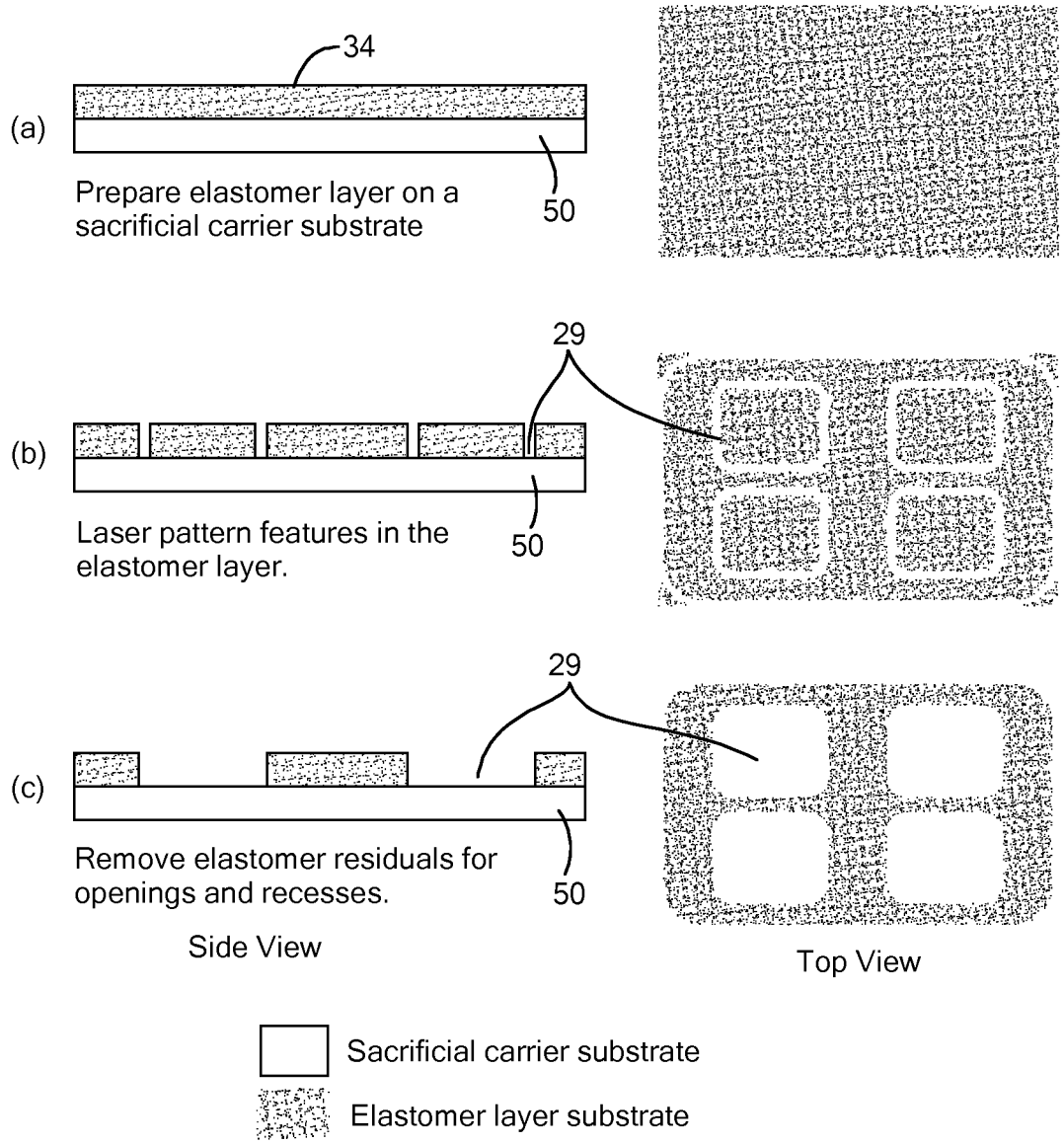
FIG. 14 graphically shows a non-reinforced electrode base layer as it is formed in accordance with other embodiments of the invention.

Optionally, the unvulcanized elastomer substrate 26 may include the noted reinforcing material 36, which also is shown in FIG. 13. As shown, the reinforcement material 36 may be added at step (i) of FIG. 13. FIG. 14 shows a similar process of forming the base layer, but without a reinforcing material 36.

Returning to FIG. 11, step 1102 also may form the cover layer. In a manner similar to the base layer, the cover layer also may be formed in an unvulcanized state and processed in a similar manner, either with or without the reinforcement material 36. Indeed, those skilled in the art can form the cover layer using a number of other techniques.

Figure 15:
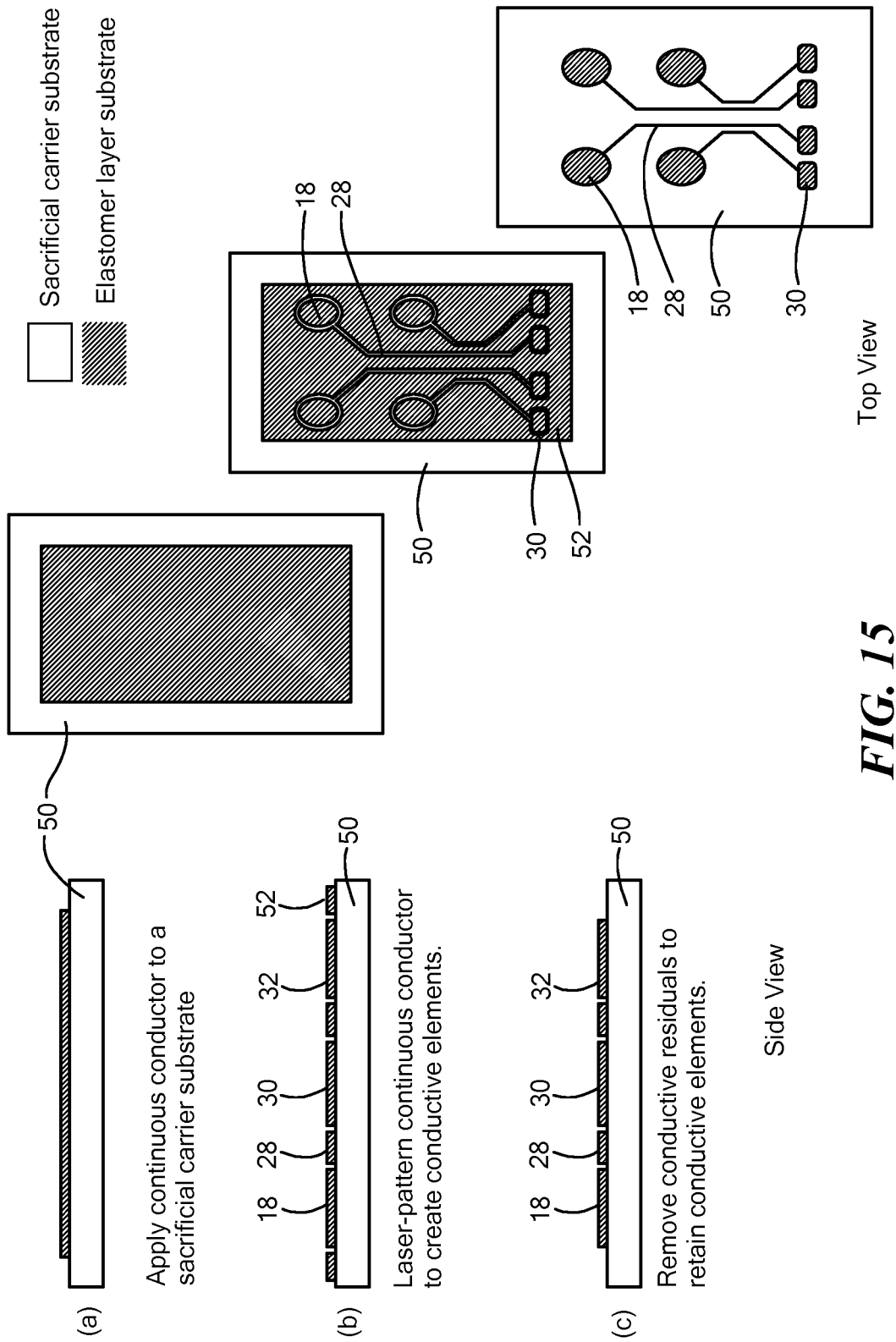
FIG. 15 graphically shows the patterning process of a conductive layer as it is formed in accordance with illustrative embodiments of the invention.

Next, the process continues to step 1104, which forms the continuous conductive elements. In this example, these elements are formed from a flat/planar layer of metal. In other embodiments, however, other materials may suffice, such as a conductive polymer, a non-flat metal layer, etc. Those skilled in the art thus can apply other materials to form the continuous conductive elements. To those ends, FIG. 15 schematically shows a process of forming the continuous conductive elements from a metal layer in accordance with illustrative embodiments of the invention. The continuous conductive element material may have a thickness of 5-50 micrometers and comprise primarily a metal (e.g., platinum, platinum-iridium, palladium).

As shown in FIG. 15, the continuous conductor (e.g., foil, strips, etc.) may be applied to a sacrificial release carrier substrate 50, such as a thermal release or UV release carrier substrate 50 (step a, FIG. 15). Step b of FIG. 15 then patterns the conductor (e.g., laser micro-machining or ablation) to form continuous conductive elements, such as the electrode sites 18, conductive interconnects 28, and conductive contacts 30. Accordingly, illustrative embodiments form high-density continuous conductive elements (e.g., 25 micrometers lines with 25 micrometers spaces or larger) to produce multi-contact electrode arrays 10 (e.g., more than 16 electrodes 18).

Those skilled in the art may use other spatial patterning technologies, such as film printing, screen printing, deposition or other method(s). Step (c) of FIG. 15 then mechanically removes residual conductive elements 52, if necessary, to achieve the desired continuous conductive elements spatially arranged on the sacrificial release carrier substrate 50. Indeed, as noted above, the electrode array components may be formed from other materials that perform the same functions and thus, discussion of specific materials and thicknesses is not intended to limit the scope of various embodiments. For example, other embodiments may use additive deposition processes with a conductive polymer, ink, or some other conductor.

Returning to FIG. 11, after forming the unvulcanized base, unvulcanized cover, and continuous conductive elements, the process may begin to assemble the overall unitary electrode body. To that end, step 1106 positions and aligns the metal layer on the base layer, and step 1108 removes the carrier substrate 50 from the metal layer. FIG. 12(*ii*) and (iii) graphically show this alignment, which preferably aligns the metal with appropriate openings 29, among other things.

Alternatively, other embodiments may align the conductive element layer with the cover layer.

Next, step 1110 positions and aligns the metal layer with openings 29 in the cover layer, while step 1112 removes the cover layer carrier substrate 50. FIG. 12 shows these two steps at (iv) and (v). Other embodiments may add additional unvulcanized layers with and/or without flat reinforcement material 36, and additional layers of continuous conductive elements. Accordingly, instead of just a single base and cover layer to be fused, the process may repeat some or all of the prior steps to add further unvulcanized layers with or without reinforcement material 36 and/or continuous conductive elements.

At this point in the process, the base and cover are ready to be fused together to form the single, integral/unitary electrode substrate/body 26 as discussed above. Specifically, step 1114 vulcanizes the assembly to create a permanent elastomer fusion (elastomer-to-elastomer welding), forming the single substrate 26. This involves applying heat and pressure, as required by the materials and application, to fuse the layers together. Among other benefits, the fusion process (v) is expected to provide electrical isolation and implanted electrode longevity. The resulting metal contacts 30 and electrode sites 18 thus are exposed as desired, although they may be recessed slightly below the rims of the openings 29 exposing them.

After completing the process, the fused unitary body 26 may be subjected to various post-processing steps, such as step (vi), which may form the electrode therapy embodiments discussed above (among others) using a curving process to form a curved electrode, cylindrical catheter electrode, nerve-cuff, conformal paddle, or other geometries. The sub-assembly from (v) therefore may be combined with other processes that those skilled in the art may use to form these noted implementations. For example, to form a nerve cuff electrode or a cylindrical catheter style electrode, the substrate 26 can be formed around a mandrel and integrated with other injection molding or centerless grinding steps.

Similarly, the post-processing step (vi) can attach wires from the lead 14 to the contact contacts 30. Among other things, step (iv) can include various types of welding (e.g., thermo compression, resistance welding, laser welding, conductive elastomers, etc.). The welding sites and exposed contact contacts 30 preferably are subsequently molded with thick elastomer insulating encapsulant to provide isolation between the contact contacts 30.

Accordingly, unlike electrode arrays having bodies formed from two or more adhered layers, illustrative embodiments form a unitary single body 26. As a result, the electrode array 10 should be more robust, particularly when subjected to anticipated forces within the human body.

Although the above discussion discloses various exemplary embodiments of the invention, it should be apparent that those skilled in the art can make various modifications that will achieve some of the advantages of the invention without departing from the true scope of the invention.

What is claimed is:

1. A method of fabricating an electrode array, the method comprising:
    forming a first unvulcanized layer;
    forming a second unvulcanized layer;
    patterning a layer of conductive material to form a plurality of electrodes;
    forming apertures in at least one of the first and second unvulcanized layers;
    coupling the electrodes with one of the first and second unvulcanized layers;
    coupling together the first and second unvulcanized layers in a manner that at least partially encapsulates the electrodes;
    vulcanizing the first and second unvulcanized layers after coupling them together, vulcanizing the first and second unvulcanized layers forming a vulcanized unitary body,
    the plurality of apertures of the vulcanized unitary body exposing the plurality of electrodes.

2. The method as defined by claim 1 further comprising:
    forming a third unvulcanized layer;
    patterning additional conductive material to form a second plurality of electrodes;
    coupling the second plurality of electrodes with one of the unvulcanized layers; and
    vulcanizing the layers after coupling them together to form the vulcanized unitary body.

3. The method as defined by claim 1 wherein vulcanizing comprises applying a thermo-mechanical process to the coupled first and second unvulcanized layers, the thermo-mechanical process including applying heat and pressure to the first and second unvulcanized layers.

4. The method as defined by claim 1 further comprising positioning a reinforcing material within one of the first and second unvulcanized layers before coupling together, the first and second unvulcanized layers comprising a material having a material tensile strength, the reinforcing material having a reinforcing tensile strength that is greater than the material tensile strength.

5. The method as defined by claim 1 wherein the first and second unvulcanized materials are chemically fused together to form the vulcanized unitary body.

6. The method as defined by claim 1 wherein the first and second unvulcanized layers comprise silicone, coupling together comprising a silicone to silicone bond.

7. The method as defined by claim 1 wherein the first and second unvulcanized layers comprise thermoplastic polyurethane, coupling together comprising a thermoplastic-polyurethane bond.

8. The method as defined by claim 1 wherein the patterning comprises laser cutting the conductive material.

9. The method as defined by claim 1 wherein the first unvulcanized layer forms a cover after coupling together, further wherein the second unvulcanized layer forms a base after coupling together.

10. The method as defined by claim 1 wherein forming a first unvulcanized layer comprises adding unvulcanized material to a sacrificial layer, the method further comprising removing the sacrificial material after coupling together.

11. The method as defined by claim 1 wherein forming apertures comprises forming apertures in both the first and second unvulcanized layers.

12. The method as defined by claim 1 further comprising:
    coupling a wire to the plurality of contacts; and
    coupling the wire to a pulse generator to electrically connect the electrodes with the pulse generator.

13. The method as defined by claim 1 wherein the unitary body is seamless.

14. The method as defined by claim 1 further comprising forming additional apertures in the vulcanized unitary body to expose at least one electrodes or to form more through-holes in the vulcanized unitary body.

* * * * *